United States Patent [19]

Krilis et al.

[11] Patent Number: 5,344,758
[45] Date of Patent: Sep. 6, 1994

US005344758A

[54] METHODS FOR DETERMINING ANTI-PHOSPHOLIPID AND ANTI-CARDIOLIPIN ANTIBODIES

[75] Inventors: Steven A. Krilis, Hunter's Hill; Hugh P. McNeill, Jannali; Colin N. Chesterman, Bellevue Hill, all of Australia

[73] Assignee: Yamasa Shoyu Kabushiki Kaisha, Japan

[21] Appl. No.: 777,521

[22] Filed: Dec. 6, 1991

[30] Foreign Application Priority Data

Apr. 6, 1990 [AU] Australia ................................ PJ9549
Sep. 7, 1990 [AU] Australia ................................ PK2186

[51] Int. Cl.$^5$ ...................... C07K 15/14; G01N 33/92; G01N 33/543; G01N 33/564
[52] U.S. Cl. ..................................... 433/4.1; 435/7.92; 435/188; 435/810; 436/518; 436/506; 436/71; 436/87; 530/359; 530/380
[58] Field of Search ............... 435/7.92, 810; 436/506, 436/518, 71, 87, 823, 829; 530/389.3, 359, 380

[56] References Cited

PUBLICATIONS

Nimpf et al. "Prothrombinase activity of human platelets is inhibited by Pzglycoprotein–I" 1986 Biochimica et Biophysica Acta 884:142–149.
E. Politz, Protides in Biological Fluids, 27, 817–820, (1980).
M. Galli et al., LANCET, 335(8705) 1544–1547, (1990).
Murakami, H., "Keio J Med", 36(3) 284–297 (1987).
Cheng, Hwee-Ming et al., "Immunological Investigations", 18(9&10) 1121–1127 (1989).
McNeil, H. P., et al. "British Journal of Haematology", 73(4) 506–513 (1989).
Loizou, S., et al. "Clin. exp. Immunol.", 80(2) 171–176 (1990).
McNeil, H. P., et al. "Thrombosis Research", 52(6) 609–619 (1988).
Hazeltine, M. et al. "The Journal of Rheumatology", 52(1) 80–86 (1988).
McNeil, H. P. et al. "Proc. Natl. Acad. Sci. USA", 87(11) 4120–4124 (Jan. 1990).

Primary Examiner—Esther L. Kepplinger
Assistant Examiner—Nancy J. Parsons
Attorney, Agent, or Firm—Wenderoth, Lind & Ponack

[57] ABSTRACT

A method for determining whether antiphospholipid antibodies are present in a sample is disclosed. The method comprises contacting the sample with a negatively charged phospholipid and with β-2-glycoprotein-I or a homolog or analog thereof and determining whether any antiphospholipid antibodies have bound to the contacted phospholipid and β-2-glycoprotein-I, wherein detection of binding of antiphospholipid antibodies to the phospholipid and β-2-glycoprotein-I, is indicative that antiphospholipid antibodies are present in the sample. Also disclosed is a method for determining whether a negatively charged phospholipid is present in a sample, a kit for use in an assay for determining whether antiphospholipid antibodies are present in a sample, a kit for use in an assay for determining whether a negatively charged phospholipid is present in a sample, a method for determining whether antiphospholipid antibodies in a sample are antibodies to an autoimmune disease or antibodies to an infectious disease and a method for determining whether antiphospholipid antibodies to an autoimmune disease and antiphospholipid antibodies to an infectious disease are present in a sample.

20 Claims, 10 Drawing Sheets

```
      1             5                      10
NH2-Gly-Arg-Thr-X-Pro-Lys-Pro-Asp-Asp-Leu-Pro-Phe-
     15            20              24
Ser-Thr-Val-Val-Pro-Leu-X-Thr-Phe-Tyr-Glu-Pro-
```

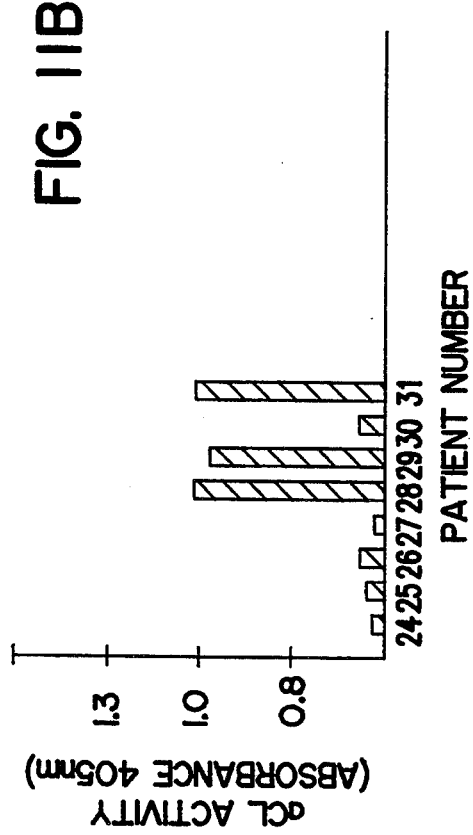
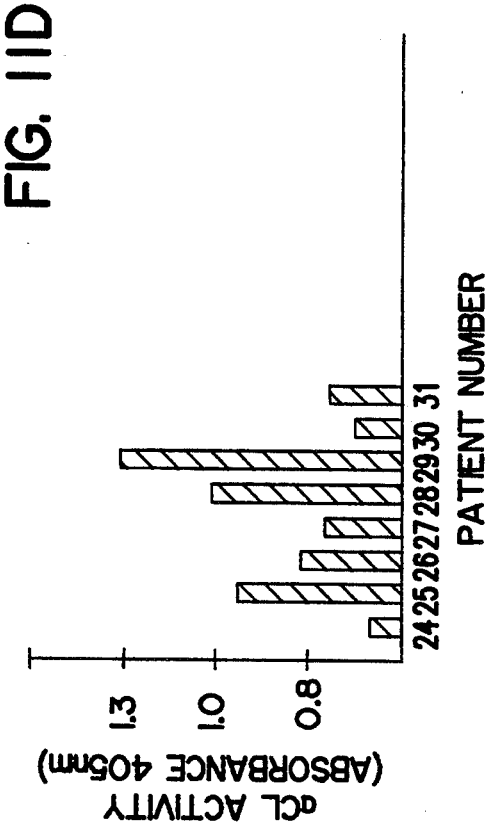
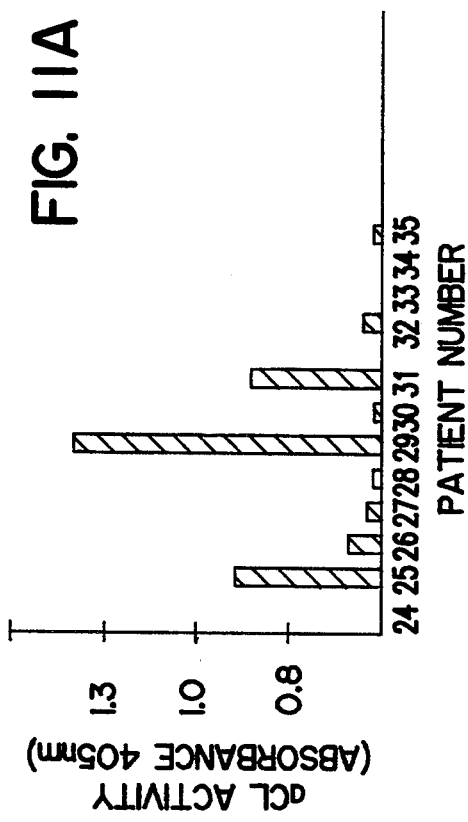
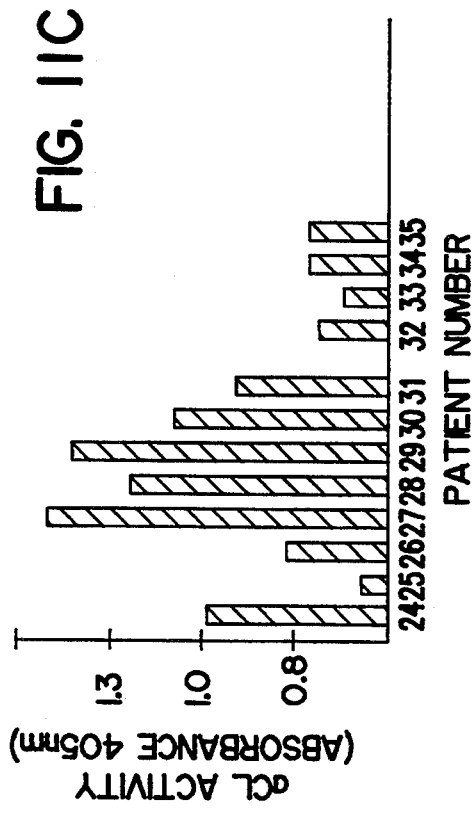

METHODS FOR DETERMINING ANTI-PHOSPHOLIPID AND ANTI-CARDIOLIPIN ANTIBODIES

TECHNICAL FIELD

This invention relates to a method and kit for determining whether antiphospholipid antibodies are present in a sample, and a method and Kit for determining whether a negatively charged phospholipid is present in a sample.

This invention also relates to a method for determining whether antiphospholipid antibodies in a sample are antibodies to an autoimmune disease or antibodies to an infectious disease and a method for determining whether antiphospholipid antibodies to an autoimmune disease and antiphospholipid antibodies to an infectious disease are present in a sample.

BACKGROUND ART

Antiphospholipid (aPL) antibodies are autoantibodies which can be detected in plasma or serum in solid phase immunoassays employing negatively charged phospholipids, most commonly cardiolipin (CL) as the antigen.

A simple 2-step procedure for purifying aPL antibodies from plasma (or serum) using sequential phospholipid affinity and cation-exchange chromatography, yielding specific immunoglobulin of >95% purity has been described. These antibodies exhibit typical binding in CL-ELISA but do not possess lupus anticoagulant (LA) activity in phospholipid dependent clotting tests. Recently, it has also been shown that plasma can be resolved by ion-exchange chromatography into fractions containing either anticardiolipin (aCL) antibodies or antibodies with LA activity, strongly suggesting that aCL and LA antibodies represent distinct aPL antibody subgroups, and appear to be directed against a different antigen.

Solid phase immunoassays to detect plasma or serum antibodies which bind phospholipid antigens (such as cardiolipin [CL]) were developed in the mid 1980's and are now available as ready to use Commercial kits, from a number of Biotechnology companies as commercial kits, and many laboratories use these, or alternatively use their own 'in house' assays. Essentially CL is coated onto the bottom of microtitre wells and serum or plasma samples added. Anticardiolipin, aPL antibodies are bound which can be detected using enzyme-linked anti-human (second) antibodies. It has been noted however, that some samples exhibit binding lower than predicted when diluted and the explanation for this is unclear. However, this gives rise the problem that some samples may be 'falsely' negative because of a dilution effect. Anti-phospholipid antibodies (aPL) detected in solid phase enzyme linked immunoassays (ELISA) employing cardiolipin (CL) as the antigert are termed anticardiolipin antibodies (aCL). aCL have been detected in patients with syphilis and other infections, in autoimmune disease, as a drug induced condition and in a percentage of the normal population.

The presence of aCL in patients with autoimmune disease confers an increased risk of arterial and venous thrombosis, recurrent spontaneous foetal loss and thrombocytopaenia. However, these clinical features are not associated with aCL occurring in syphilis or other infections.

This suggests that there is some qualitative difference between aCL found in the two groups. Thus there is a need for a method for determining whether antiphospholipid antibodies in a sample are antibodies to an autoimmune disease or antibodies to an infectious disease as well as for a method for determining whether antiphospholipid antibodies to an autoimmune disease and antiphospholipid antibodies to an infectious disease are present in a sample.

OBJECTS OF THE INVENTION

It is an object of the invention to provide an assay for determining whether an antiphospholipid antibody (as herein defined), is present in a sample.

It is another object of the invention to provide an assay for determining whether a negatively charged phospholipid is present in a sample.

It is a further object of the invention to provide kits for use in the assays according to the invention.

It is yet a further object of this invention to provide a method for determining whether antiphospholipid antibodies in a sample are antibodies to an autoimmune disease or antibodies to an infectious disease.

Another object is to provide a method for determining whether antiphospholipid antibodies to an autoimmune disease and antiphospholipid antibodies to an infectious disease are present in a sample.

DISCLOSURE OF THE INVENTION

As used herein the term antiphospholipid antibodies, refers to antiphospholipid antibodies which generally bind all negatively charged phospholipids, particularly cardiolipin, but which do not exhibit lupus anticoagulant activity.

Antiphospholipid (aPL) antibodies which exhibit binding in cardiolipin enzyme linked immunoassays (CL-ELISA), can be purified to >95% purity using sequential phospholipid affinity and ion-exchange chromatography.

The present inventors have found that when aPL antibody containing fractions derived from ion-exchange chromatography of plasma are applied to phosphatidyl-serine (PS) or CL affinity columns, there is no binding of the antibody despite the fact that when plasma containing these antibodies is applied to these columns, aPL antibodies can be purified. Binding to the phospholipid antigen will only occur if normal human plasma, serum or bovine serum is present, suggesting the binding of aPL antibodies to CL requires the presence of a plasma/serum cofactor. Addition of normal (aPL antibody negative) plasma to the ion-exchange fractions results in aPL binding to the columns, supporting this hypothesis.

Using sequential phospholipid affinity, gel-filtration and ion-exchange chromatography, the inventors have purified this cofactor to homogeneity and have shown that the binding of aPL antibodies to CL requires the presence of this cofactor in a dose-dependent manner.

N-terminal region sequence analysis of the molecule has identified the cofactor as beta-2-glycoprotein-I-($\beta$-2GPI) (apolipoprotein H), a plasma protein Known to bind to anionic phospholipids. These findings indicate that the presence of $\beta$-2GPI or a homolog or analog thereof is an absolute requirement for antibody/phospholipid interaction, suggesting bound $\beta$-2GPI forms the antigen to which aPL antibodies are directed.

The present invention is based on the discovery that the binding of aPL antibodies in plasma, in a standard assay using negatively charged phospholipids, in particular CL, can be significantly enhanced by the addition of purified $\beta_2$-glycoprotein-I, to the assay. This enhancement in sensitivity is most marked at dilutions of 1:50, this being the standard dilution in most assays.

According to a first embodiment of this invention there is provided a method for determining whether antiphospholipid antibodies (as herein defined) are present in a sample, comprising:

contacting the sample with a negatively charged phospholipid and with $\beta$-2-glycoprotein-I or a homolog or analog thereof; and determining whether any antiphospholipid antibodies have bound to the contacted phospholipid and $\beta$-2-glycoprotein-I.

The detection of binding of aPL antibodies to the phospholipid and $\beta$-2GPI indicates that aPL antibodies are present in the sample.

The sample can be a blood fraction, such as serum or plasma, from any mammal.

Any negatively charged phospholipid, such as cardiolipin, phosphatidyl inosityl, phosphatidyl serine, phosphatidyl glycerophosphate, phosphatidic acid, or homologs or analogs thereof can be used in the method of this embodiment. Typically, cardiolipin will be employed.

According to a second embodiment of this invention there is provided a method for determining whether a negatively charged phospholipid is present in a sample, comprising:

contacting the sample with antiphospholipid antibodies (as herein defined) to the phospholipid and with $\beta$-2-glycoprotein-I or a homolog or analog thereof; and determining whether negatively charged phospholipid has bound to the contacted antibodies and $\beta$-2-glycoprotein-I.

The detection of binding of negatively charged phospholipid with $\beta$-2GPI and with aPL antibodies, indicates that the negatively charged phospholipid is present in the sample.

The sample can be whole blood, or a fraction thereof, such as serum or plasma from any mammal. The assays according to the invention are particularly applicable to humans.

In the methods of the invention, the negatively charged phospholipid or aPL antibody will typically be immobilized, by known techniques, onto a suitable solid phase, such as affinity column packing material, or a plastic surface such as a microtitre plate or a dipstick.

Appropriate affinity column packing materials include, a beaded agarose matrix, polyacrylamide, glass, cellulose or cross linked dextran.

Suitable plastic surfaces include polymethylacrylate, polystyrene, polyethylene, polyterepthalate, ethylene glycol, polyester, polypropylene, and the like. Generally any standard microtitre plate may be used.

Alternatively the solid phase may be in the form of a get or matrix into which the aPL antibody or phospholipid, optionally together with $\beta$-2GPI is incorporated.

In another form, in the method according to the first embodiment the phospholipid, optionally together with $\beta$-2GPI may be incorporated into liposomes or micelles.

The $\beta$-2GPI may be derived from any mammal. Desirably it is in substantially pure form. $\beta$-2GPI may be purified from serum or plasma by known techniques for example by phospholipid chromatography. However, $\beta$-2GPI produced by recombinant DNA techniques, or peptide synthesis may be used.

The $\beta$-2GPI, may be contacted with the sample to be tested according to the method of the first or second embodiment, before or after the sample is contacted with the negatively charged phospholipid or aPL antibody. Alternatively in the assay according to the first embodiment the $\beta$-2GPI may be immobilized with the antigert on a solid phase or incorporated into liposomes or micelles.

The binding of the antiphospholipid antibodies to the phospholipid and $\beta$-2-glycoprotein-I may be determined by any suitable method known in the art including by way of example only: ELISA, radioimmunoassay (RIA), immunofluorescence, chemiluminescence and nephelometry.

Typically, standard ELISA techniques are employed using labelled antibody or antigen. The label can be an enzyme, fluorophore, chemiluminescent material, radioisotope, or coenzyme. Generally enzyme labels such as alkaline phophatase, or beta galactosidase are employed together with their appropriate substrates. The enzyme/substrate reaction can be detected by any suitable means such as spectrophotometry.

Where the phospholipid is incorporated into liposomes, a liposome lysis assay may be used as described in Bonerji B., Lyon J. A., Alving C. R., Biochem. Biophys Acta 1982, 689:319-328 and Alving C. R., Richards R. L., Guirgius A. A., J. Immunology, 1977, 118:342.

According to a third embodiment of the invention there is provided a kit for use in an assay for determining whether antiphospholipid antibodies (as herein defined), are present in a sample, comprising:

a) $\beta$-2GPI or homolog or analog thereof, and
b) a negatively charged phospholipid.

The kit may further comprise, c) means for detecting binding of antiphospholipid antibodies present in the test sample, to $\beta$-2GPI and the negatively charged phospholipid.

Any appropriate means for detecting binding of the antibodies may be employed such as a labelled anti-human antibody wherein the label may be an enzyme, fluorophore, chemiluminescent material radioisotope, coenzyme. Generally the label used will be an enzyme.

According to a fourth embodiment of the invention there is provided a kit for use in an assay for determining whether a negatively charged phospholipid is present in a sample, comprising:

a) $\beta$-2GPI or homolog or analog thereof, and
b) antiphospholipid antibodies (as herein defined).

The Kit may further comprise, c) means for detecting binding of the antiphospholipid antibodies to $\beta$-2GPI and negatively charged phospholipid present in the test sample.

Any suitable means for detecting binding of aPL antibodies may be employed. Typically a labelled aPL antibody is used, wherein the label is an enzyme. Other suitable labels which can be used include, a fluorophore, chemiluminescent material, radioisotope or coenzyme.

An advantage of the assays according to the invention is that addition of excess $\beta$-2GPI to a sample enables optimal binding of aPL antibodies to negatively charged phospholipid, leading to significant increases In sensitivity as compared to assays routinely used, It follows as a result of this increased sensitivity that samples which are "negative" in a routine aPL assay may be found to be positive in the assay according to the invention, thus minimising "false negatives"

The detection of aPL antibodies is of considerable clinical importance since their presence in the body is associated with thrombosis, foetal loss and other clinically significant syndromes. The enhancement of sensitivity of assays for these antibodies is thus of major clinical relevance.

On investigating the binding specificities of antiphospholipid antibodies (aCL) purified from patients with autoimmune disease and from patients with infections to phospholipid-binding plasma protein, $\beta_2$-glycoprotein I ($\beta_2$-GPI) the present inventors have discovered that the binding specificities of aCL from patients with autoimmune disease are different from aCL from patients with infections. Specifically, the inventors found:

aCL antibodies in 11 out 12 patients with autoimmune disease only bound cardiolipin (CL) in the presence of $\beta_2$-GPI.

In contrast, aCL purified from patients with malaria, infectious mononucleosis, tuberculosis, hepatitis A and syphilis bound CL without $\beta_2$-GPI.

Thrombotic complications appear to be associated with aCL occurring in autoimmune disease but not with aCL associated with infections. The present inventors postulate that this increased risk of thrombosis in the autoimmune group may be due to the presence of aCL antibodies that bind CL in association with $\beta_2$-GPI, a plasma protein with anticoagulant activity.

According to a fifth embodiment of this invention there is provided a method for determining whether antiphospholipid antibodies in a sample are antibodies to an autoimmune disease or antibodies to an infectious disease, which method comprises:
  (i) contacting a portion of the sample with a negatively charged phospholipid and determining a first amount of antiphospholipid antibodies in the sample without contacting the portion of the sample with $\beta$-2-glycoprotein-I or an analog or homolog thereof:
  (ii) contacting another portion of the sample with a negatively charged phospholipid and with $\beta$-2-glycoprotein-I or an analog or homolog thereof and determining a second amount of antiphospholipid antibodies in the sample:
  (iii) determining whether antiphospholipid antibodies determined in the sample are antiphospholipid antibodies to an autoimmune disease or antibodies to an infectious disease by comparing the first amount to the second amount wherein antiphospholipid antibodies determined in the sample are to an autoimmune disease when the first amount is substantially less than the second amount and antiphospholipid antibodies determined in the sample are to an infectious disease when the first amount is substantially greater than the second amount.

According to a sixth embodiment of this invention there is provided a method for determining whether antiphospholipid antibodies to an autoimmune disease and antiphospholipid antibodies to an infectious disease are present in a sample, which method comprises:
  (i) contacting a portion of the sample with a negatively charged phospholipid and determining a first amount of antiphospholipid antibodies in the sample without contacting the portion of the sample with $\beta$-2-glycoprotein-I or an analog or homolog thereof;
  (ii) contacting another portion of the sample with a negatively charged phospholipid and with $\beta$-2-glycoprotein-I or an analog or homolog thereof and determining a second amount of antiphospholipid antibodies in the sample;
  (iii) determining whether antiphospholipid antibodies determined in the sample are antiphospholipid antibodies to an autoimmune disease and antibodies to an infectious disease by comparing the first amount to the second amount wherein antiphospholipid antibodies determined in the sample are to an autoimmune disease and to an infectious disease when the first amount is substantially the same as the second amount.

The following remarks apply to the fifth and sixth embodiments.

What is meant by the first amount being substantially less than the second amount is that the second amount is at least about 1.1 times greater than the first amount (and the second amount can be 100,000 times greater than the first amount and more). What is meant by the first amount is substantially greater than the second amount is that the first amount is at least about 1.1 times greater than the second amount (and the first amount can be 100,000 times greater than the second amount and more).

What is meant by the first amount being substantially the same as the second amount is that the first amount is greater than 0.9 times the second amount and less than about 1.1 times the second amount. The first amount in this instance can be substantially equal to the second amount.

The sample can be whole blood or a fraction thereof, such as serum or plasma from any mammal. The methods according to the invention are particularly applicable to body fluids from humans.

In the methods of the invention, the negatively charged phospholipid will typically be immobilised, by Known techniques, onto a suitable solid phase, such as affinity column packing material, or a plastic surface such as a microtitre plate or a dipstick.

Appropriate affinity column packing materials include, a beaded agarose matrix, polyacrylamide, glass, cellulose or cross linked dextran.

Suitable plastic surfaces include polymethylacrylate, polystyrene, polyethylene. polyterepthalate, ethylene glycol, polyester, polypropylene, and the like. Generally any standard microtitre plate may be used.

Alternatively the solid phase may be in the form of a gel or matrix into which the negatively charged phospholipid and, in method steps (ii), $\beta$-2GPI are incorporated.

In another form, in the methods according to the fifth and sixth embodiments in method steps (ii), the phospholipid together with $\beta$-2GPI may be incorporated into liposomes or micelles.

The $\beta$-2GPI may be derived from any mammal. Desirably it is in substantially pure form. $\beta$-2GPI may be purified from serum or plasma by known techniques for example by phospholipid chromatography. However, $\beta$-2GPI produced by recombinant DNA techniques, or peptide synthesis may be used.

In method steps (ii), the $\beta$-2GPI, may be contacted with the sample to be tested before or after the sample is contacted with the negatively charged phospholipid. Alternatively, in method steps (ii) the $\beta$-2GPI may be immobilized with the antigen on a solid phase or incorporated into liposomes or micelles.

The binding of the antiphospholipid antibodies to the phospholipid (and β-2-glycoprotein-I in method steps (ii)) may be determined by any suitable method known in the art including by way of example only: ELISA, radioimmunoassay (RIA), immunofluorescence, chemiluminescence and nephelometry.

Typically, standard ELISA techniques are employed using labelled antibody or antigen. The label can be an enzyme, fluorophore, chemiluminescent material, radioisotope, or coenzyme. Generally enzyme labels such as alkaline phophatase, or beta galactosidase are employed together with their appropriate substrates. The enzyme/substrate reaction can be detected by any suitable means such as spectrophotometry.

Where the phospholipid is incorporated into liposomes, a liposome lysis assay may be used as described in Bonerji B., Lyon J. A., Alving C. R., Biochem. Biophys Acta 1982, 689:319–328 and Alving C. R., Richards R. L., Guirgius A. A., a. Immunology, 1977, 118:342.

Any appropriate means for detecting binding of the aPL antibodies may be employed such as a labelled anti-human antibody wherein the label may be an enzyme, fluorophore, chemiluminescent material radioisotope, coenzyme. Generally the label used will be an enzyme.

in method steps (ii) the addition of excess β-2GPI to a sample enables optimal binding of aPL antibodies to negatively charged phospholipid, leading to significant increases in sensitivity as compared to assays routinely used.

BRIEF DESCRIPTION OF THE DRAWINGS

FIG. 6 (b) illustrates binding in the standard CL-ELISA and modified CL-ELISA of serial dilutions of aCL antibody positive plasma.

FIGS. 11 A–D show results of modified CL-ELISA performed on patients with aCL associated with autoimmune disease, A and B=no $\beta_2$-GPI added, C and D=$\beta_2$-GPI added;

FIGS. 11A and 11C: patient numbers 24–31=IgG, 32–35=polyvalent; and

FIGS. 11B and 11D: patient numbers 24–31=IgA; and

BEST MODE AND OTHER MODES OF CARRYING OUT THE INVENTION

Figure 1:
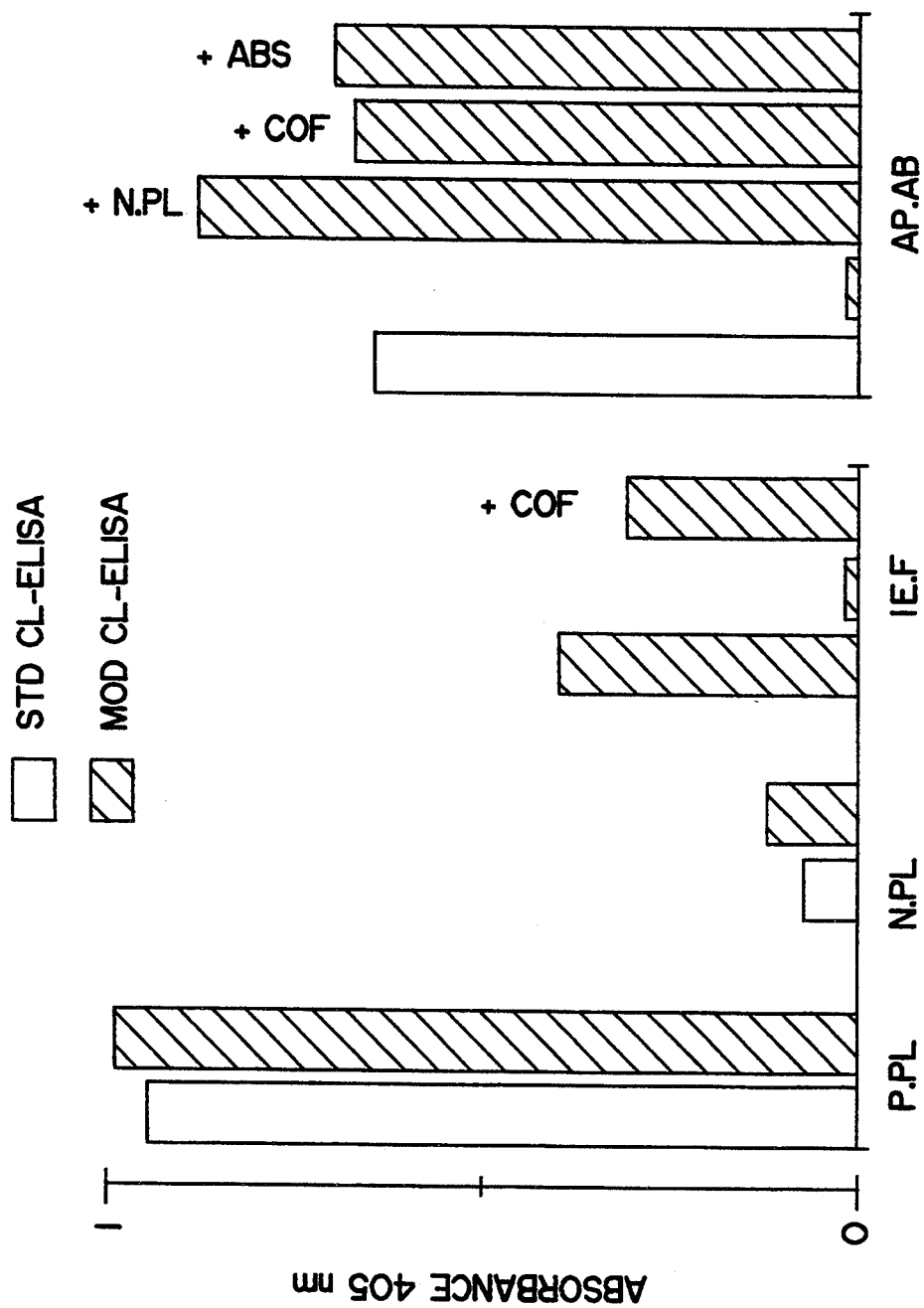
FIG. 1 illustrates binding of various samples in standard and modified CL-ELISA. aCL antibody containing ion-exchange fractions (IE.F); affinity purified aCL antibodies (AP.AB); normal plasma (N.PL); adult bovine serum (ABS); purified cofactor (COF); patient plasma (P.PL). ABS and COF are negative when tested alone (not shown).

The method of the first embodiment will now be described with reference to the detection of aPL antibodies in a sample.

β-2-glycoprotein-I is purified from normal human plasma or serum by phospholipid chromatography.

A stock solution of $\beta_2$ GPI is prepared and added to plasma or serum samples to obtain a final concentration of 50 μg/ml in the diluted sample (usually 1:50 in assay buffer).

The samples are then assayed for aPL antibodies by a CL-ELISA assay as follows.

CL is coated onto the bottom of microtitre plates by adding CL to the plate in a solution of ethanol. The ethanol is evaporated off leaving a coating of CL on the surface of the plate.

The coated microtitre plates are incubated with 1:50 dilution of serum or plasma samples as prepared above, washed, and incubated with alkaline phosphatase linked anti-human antibodies. The plates are then washed a second time and incubated with substrate. The products of the enzyme reaction are detected by spectrophotometry.

The method of the invention will now be described with reference to the detection of negatively charged phospholipid in a sample, by means of a double antibody sandwich assay.

β-2-glycoprotein-I is prepared and added to serum or plasma samples as described above to obtain a final concentration of 50 μg/ml in the diluted sample (usually 1:50 in assay buffer). aPL antibody is adsorbed onto a microtitre plate, and serum or plasma sample is added in 1:50 dilution. The plates are washed and incubated with alkaline phosphatase linked aPL antibodies. The plates are then washed and incubated with substrate.

The products of the enzyme reaction are detected by spectrophotometry.

A method for determining whether antiphospholipid antibodies in a sample are antibodies to an autoimmune disease and/or antibodies to an infectious disease may be carried out in the following way.

Firstly, one determines antiphospholipid antibodies in the sample by analysing a portion of the sample by contacting the portion with a negatively charged phospholipid without contacting the portion of the sample with β-2-glycoprotein-I or an analog or homolog thereof and determining the amount (termed "the first amount") of antiphospholipid antibodies in the sample.. Typically, this determination is carried out using a CL enzyme-linked immunosorbent assay (ELISA). CL is coated onto the bottom of microtitre plates by adding CL to the plate in a solution of ethanol. The ethanol is evaporated off leaving a coating of CL on the surface of the plate. The plates are blocked with milk powder 1/0.3% gelatin in PBS. The coated microtitre plates are incubated with serum or plasma samples at a dilution of 1:50 in assay buffer, washed, and incubated with alkaline phosphatase linked anti-human antibodies. The plates are then washed a second time and incubated with substrate. The products of the enzyme reaction are detected by spectrophotometry.

Secondly, one determines antiphospholipid antibodies in the sample using a modified CL enzyme-linked immunosorbent assay (modified ELISA). Generally, this involves contacting another portion of the sample with a negatively charged phospholipid and with β-2-glycoprotein-I or an analog or homolog thereof and determining the amount (termed "the second amount") of antiphospholipid antibodies in that portion of the sample. More specifically, β-2-glycoprotein-I is purified from normal human plasma or serum by phospholipid chromatography. A stock solution of $\beta_2$GPI is prepared and added to a plasma or serum sample to obtain a final concentration of 50 μg/ml in the diluted sample (usually 1:50 in assay buffer). The sample is then assayed for aPL antibodies by a CL-ELISA assay as follows. CL is coated onto the bottom of microtitre plates by adding CL to the plate in a solution of ethanol. The ethanol is evaporated off leaving a coating of CL on the surface of the plate. The plates are blocked with milk powder 1%/0.3% gelatin in PBS. The coated microtitre plates are incubated with 1:50 dilution of serum or plasma samples as prepared above, washed, and incubated with alkaline phosphatase linked anti-human antibodies. The plates are then washed a second time and incubated with substrate. The products of the enzyme reaction are detected by spectrophotometry.

It is then determined whether antiphospholipid antibodies determined in the sample are antiphospholipid antibodies to an autoimmune disease or antibodies to an infectious disease by comparing the first amount to the second amount. Antiphospholipid antibodies determined in the sample are to an autoimmune disease when the first amount is substantially less than the second amount and antiphospholipid antibodies determined in the sample are to an infectious disease when the first amount is substantially greater than the second amount.

Alternatively, it is determined whether antiphospholipid antibodies determined in the sample are antiphospholipid antibodies to an autoimmune disease and antibodies to an infectious disease by comparing the first amount to the second amount wherein antiphospholipid antibodies determined in the sample are to an autoimmune disease and to an infectious disease when the first amount is substantially the same as the second amount.

The invention will now be described by reference to the following non-limiting examples.

EXAMPLE 1

Purification of aPL (aCL) antibodies and plasma cofactor

Plasma and patients

Citrated platelet free plasma was prepared by adding freshly drawn blood from venepuncture into tubes containing 1/10 final volume 0.11M tri-sodium citrate, immediate centrifugation at 2,500 g for 15 minutes and filtration through a 0.22 um Millipore Millex filter. aCL antibodies were purified from 2 patients with the Antiphospholipid Syndrome whose plasma contained high levels of aCL antibodies and strong LA activity. Plasma from 2 further patients with systemic lupus erythematosus but without histories of thrombosis were subjected to ion-exchange chromatography. The plasma cofactor was purified from a normal healthy 31 year old male whose plasma was negative for aCL antibodies and LA activity.

Ion-exchange Chromatography of patient plasma

Patient plasma was extensively dialysed against 0.05M acetate 0.05M NaCl buffer pH 4.8, centrifuged, then run on a Sepharose Fast Flow cation exchange column (Pharmacia) using a Pharmacia Fast Protein Liquid Chromatography (FPLC) system with a 1500 ml linear gradient of 0–100% eluting buffer (0.05M acetate 0.65M NaCl pH 5.2) over 5 hours as previously described. Fractions were assayed for aCL antibodies using a standard CL-ELISA and aCL antibody positive fractions were dialysed against 0.01M phosphate buffered 0.15M saline pH 7.2 (PBS) (Dulbecco A).

CL-Affinity Chromatography

A modification of the previously described method for PS affinity chromatography was used. 5.6 mg CL in ethanol (Sigma) was placed in a glass scintillation vial and the solvent evaporated under a stream of nitrogen. 2.32 mg cholesterol (BDH Chemicals) and 0.44 mg dicetyl phosphate (Sigma) were added and the lipids redissolved in chloroform. The solvent was again evaporated, 500 ul ethanol added, the vial capped and immersed in boiling water and swirled until the lipids were dissolved. 5 mls of a 15% acrylamide 5% BIS (Biorad) solution were added and the lipid/acrylamide mixture vigorously mixed by vortexing then rapidly polymerized by adding 100 ul ammonium persulphate (140 mg/ml), 2.5 ul TEMED (both from Biorad), then left at room temperature overnight. The rigid gel was homogenized using a hand operated loose fitting teflon pestel and loaded into an empty Pharmacia FPLC HR 10/10 glass column and equilibrated with 0.01M phosphate 0.05M NaCl pH 7.2. Plasma was diluted 1:5 final volume with this buffer and infused through the column at 0.5 mls/min, after which the column was washed at 0.8 mls/min until the absorbance at 280 nm of the fall-through was <0.01 units. A 40 ml linear gradient from 0–100% of eluting buffer (0.01M phosphate 1.0M NaCl pH 7.2) over 50 minutes was applied and eluted fractions containing protein were collected. Ion-exchange fractions were applied undiluted and chromatographed as above.

Standard aCL antibody immunoassay

An ELISA for aCL antibodies with minor modifications, as described in McNeil et al Thromb. Res. 52:

609–619, was used. When using polyvalent second antibody, serial dilutions of a Known positive plasma were included on each plate. The aCL antibody level of the test samples was expressed in aCL antibody units with 100 units being the absorbance at 405 nm of the positive sample at 1:50 dilution.

Modified aCL antibody immunoassay

The above standard CL-ELISA was modified as follows. 1% milk powder (Diploma)/0.3% gelatin (Ajax)/PBS was used for the blocking step, samples were added diluted in 0.3% gelatin/PBS, and the second antibody was diluted in 1% bovine serum albumin (BSA)/PBS instead of 10% adult bovine serum (ABS)/PBS which was used in each of the above steps in the standard assay. All other details remained identical to the standard CL-ELISA described above.

Affinity purification of aCL antibodies

Plasma from patients with high levels of aCL antibodies was chromatographed on the CL-affinity column as described above. The protein eluted from this column was dialysed overnight against 0.05M acetate 0.05M NaCl pH 4.8, then applied to a Mono-S cation-exchange column (Pharmacia) using a FPLC system. A 15 ml linear gradient from 0–100% of eluting buffer 0.05M acetate 0.65M NaCl pH 5.2 over 30 minutes was applied and highly purified aCL antibodies eluted at 30% eluting buffer.

Purification of the plasma cofactor

Normal plasma was chromatographed on the CL-affinity column as described above. Fractions containing the eluted protein were concentrated in an Amicon concentrator using a YM 10 membrane and 200 kPa pressure, then dialysed against 0.01M phosphate 1M NaCl pH 7.2 and further concentrated to 200 ul in a Micro-Pro-DiCon dialysing concentrator (Bio-Molecular Dynamics) using a PA-10 membrane. The concentrated CL-column eluant was applied to a Pharmacia Superose 12 10/30 gel-filtration column operating with a FPLC system at 0.4 mls/min in a buffer of 0.01M phosphate 1M NaCl pH 7.2. Fractions from this column which were found to have cofactor activity (as described in the Results section) were pooled and dialysed overnight against 0.05M acetate 0.05M NaCl pH 4.8 then applied to a Pharmacia Mono-S cation-exchange column and eluted with 0.05M acetate 0.65M NaCl in an identical fashion described above for the purification of aCL antibodies. Fractions found to have cofactor activity were pooled and dialysed against PBS, then stored in aliquots at $-70°$ C.

Amino Acid Sequencing

Automated Edman degradation of purified cofactor was performed using an Applied Biosystems sequencer (model 477A) equipped with an on-line phenylthiohydantoin amino acid analyzer (model 120A). Total amino acid derivatives from the sequencer were injected onto the liquid chromatograph using a modified sample transfer device described elsewhere. Polybrene was used as a carrier.

Heparin Affinity Chromatography aCL antibody positive plasma, or affinity purified aCL antibody, and/or purified cofactor were applied to a column packed with 40 mls of heparin-sepharose CL-4B (Pharmacia) in 0.01M phosphate 0.05M NaCl pH 7.2 buffer and bound protein was eluted with 0.01M phosphate 1M NaCl pH 7.2.

Other methods

Samples for SDS-PAGE were run on a 5–15% linear gradient gel with a 3% stacking gel. After electrophoresis the gel was stained with Coomassie Blue. Protein determination used the method of Lowry. Vitamin K-dependent coagulation factor depleted plasma was prepared by mixing 0.1 ml of 50% aluminium hydroxide suspension (BDH Chemicals) with 1 ml of plasma and inverting the tube every minute for 15 minutes before centrifuging the precipitate.

EXAMPLE 2

CL-affinity chromatography Of aCL antibody containing ion-exchange fractions from plasma As previously indicated, plasma containing aCL antibodies and LA activity can be separated into subgroups by cation-exchange chromatography. When aCL antibody containing fractions were infused through the CL-affinity column, there was no binding with the column fall-through containing equivalent amounts of aCL antibody as the applied fraction. When normal plasma was added to the ion-exchange fractions In a ratio of 1:10 vol/vol and the mixture infused through the CL-affinity column, approximately 30% of the applied aCL antibodies were absorbed to and could be eluted from the column (Table 1). Normal plasma which had been mixed with aluminium hydroxide to remove vitamin K-dependent coagulation factors also produced a similar effect. Finally, a fraction derived from normal plasma was purified (see below) and addition of this 'cofactor' fraction (protein concentration 200 ug/ml) in a ratio of 1:5 vol/vol resulted in the absorption of 74% of the applied aCL antibodies.

EXAMPLE 3

Binding of aCL antibody containing ion-exchange fractions and affinity purified aCL antibodies in a modified aCl antibody immunoassay The results obtained in example 2 suggest a plasma dependency for the binding of aCL antibodies to CL in the affinity column. However, these aCL antibody containing fractions, and affinity purified aCL antibodies exhibit typical binding in standard solid phase CL immunoassays in the absence of plasma. These assays employ bovine serum as the blocking agent and diluent which could conceivably also contain the plasma factor necessary for antibody binding to CL. To test this, the bovine serum was replaced with gelatin as the diluent and milk powder/gelatin as the blocking agent. When aCL antibody containing ion-exchange fractions or affinity purified aCL antibodies were tested in this modified CL immunoassay, there was no binding at all. At 1:50 dilution, aCL antibody positive plasma exhibited identical binding as in the standard CL-ELISA and normal plasma was negative. Binding of antibodies in the ion-exchange fractions or affinity purified preparations did occur if normal plasma was added at dilution. An identical effect was also seen if bovine serum was added to these fractions (FIG. 1). Thus purified aCL fractions will bind in the standard CL-ELISA since the cofactor is provided by bovine serum.

This modified CL-ELISA provided a convenient method to detect cofactor activity in fractions derived from normal plasma by testing samples containing a mixture of affinity purified aCL antibodies and the fraction containing an unknown amount of cofactor. In the absence of cofactor, the affinity purified aCL antibodies would not bind and any binding was evidence of cofactor activity in the test fraction. As described below, the cofactor activity was purified from normal plasma, and the addition of this fraction to affinity purified aCL antibodies or aCL antibody containing ion-exchange fractions resulted in binding of these antibodies in the modified CL-ELISA (FIG. 1).

In the affinity chromatography system, aCL antibodies contained in fractions derived from ion-exchange of plasma did not bind to immobilised CL despite doing so when present in plasma, but binding did occur if normal plasma was added to the ion-exchange fraction. This was the first suggestion that a plasma cofactor was involved in aCL antibody-CL interactions and this has been confirmed by isolating this cofactor activity to a single plasma protein. β-2GPI (table 1). Having demonstrated this requirement, it was problematic why these ion-exchange fractions bound CL in the standard CL-ELISA. One explanation was that the cofactor or a similar molecule was also present in the bovine serum diluent used in the immunoassay. This was confirmed by modifying the CL-ELISA, omitting bovine serum and using gelatin as the diluent. In this assay, aCL antibody containing ion-exchange fractions and affinity purified aCL antibodies did not bind CL unless normal plasma or bovine serum was added (FIG. 1). Once again, in this system, the cofactor activity was isolated to β-2GPI. This was a consistent finding in 11 separate aCl antibody containing ion-exchange fractions from 4 patients consecutively studied, and 3 affinity purified aCL antibody preparations [2 IgG and 1 IgM] (data not shown).

EXAMPLE 4

Purification and identification of the cofactor in normal plasma

Figure 2:
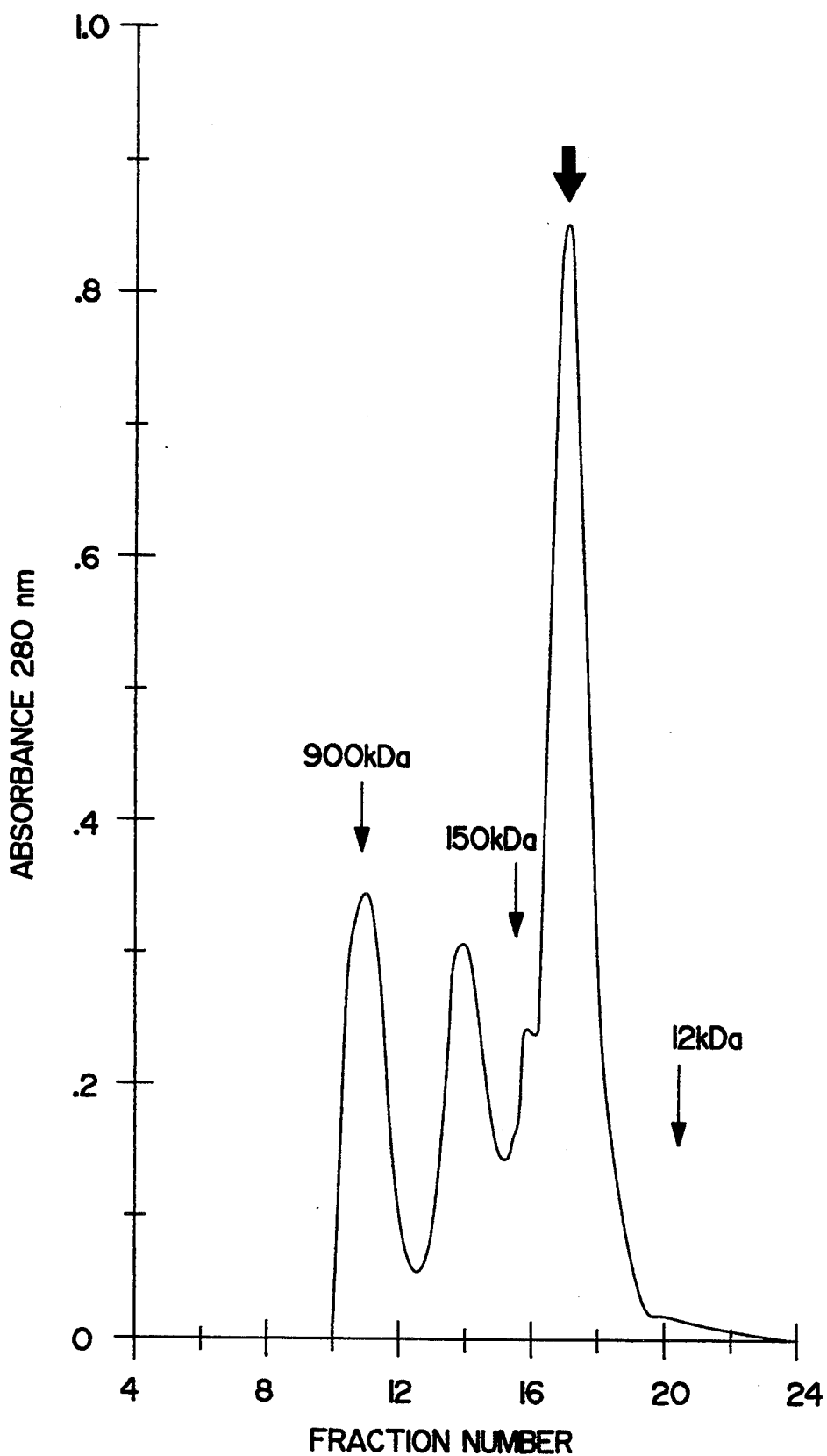
FIG. 2 illustrates gel-filtration on a Pharmacia Superase 12 HR 10/30 column of the eluant from CL affinity column chromatography of normal plasma. Buffer: 0.01M phosphate 1M NaCl. Cofactor activity was detected in the large peak indicated by the bold arrow.
Figure 3:
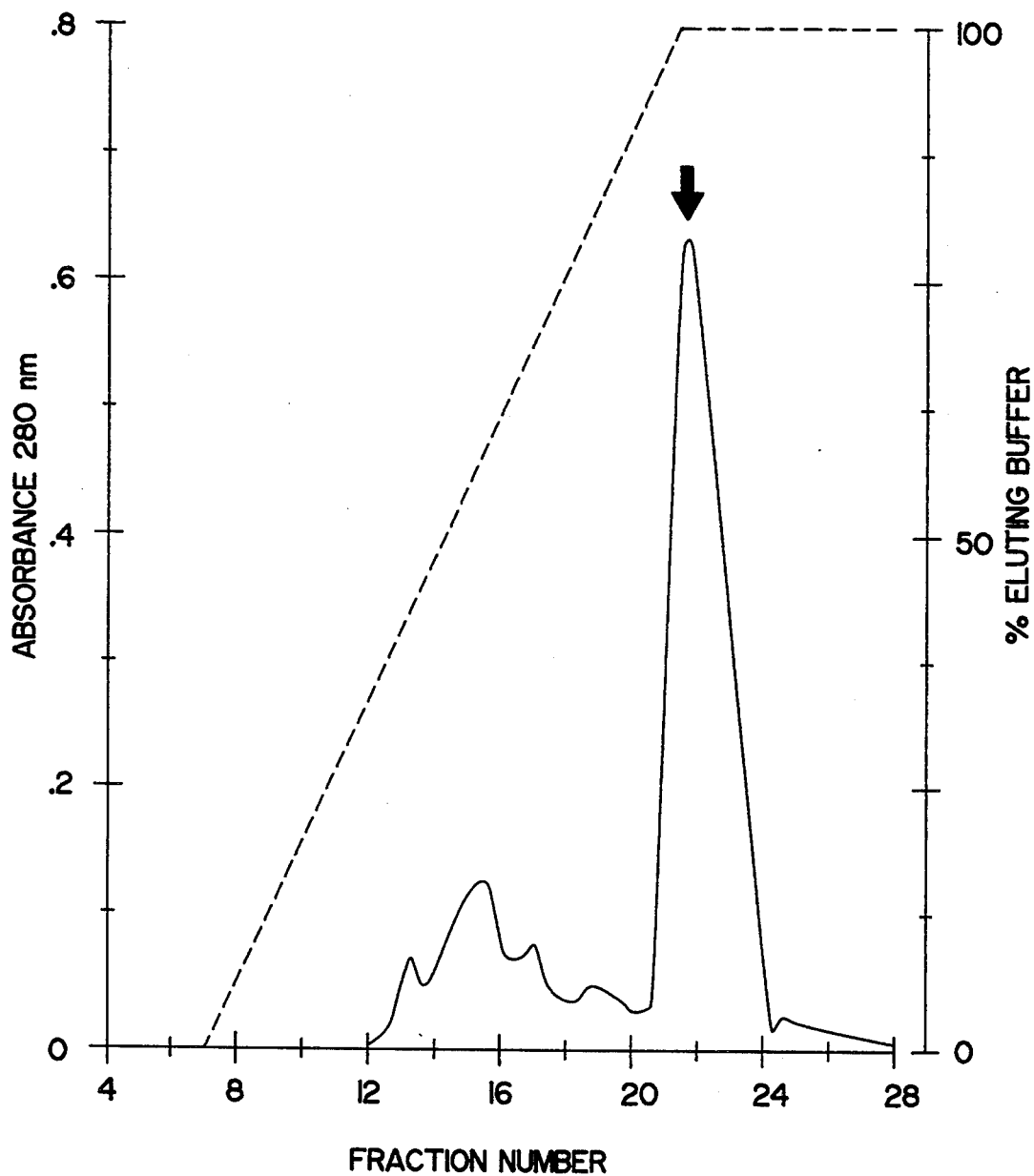
FIG. 3 illustrates cation-exchange on a Pharmacia Mona S HR 5/5 column of the cofactor containing fractions from FIG. 2. Starting buffer: 0.05M acetate 0.05M NaCl pH 4.8. Eluting buffer: 0.05M acetate 0.65M NaCl pH 5.2. Broken line; eluting buffer gradient. Cofactor activity was detected in the late peak indicated by the bald arrow.

Normal plasma was chromatographed on the CL-affinity column and the fractions were tested for cofactor activity as described above using the modified CL-ELISA. Cofactor activity was found in the eluted protein, indicating the factor bound to anionic phospholipid even in the absence of aCL antibodies. These fractions were concentrated and chromatographed on a Superose 12 gel-filtration column in 1M NaCl buffer. Cofactor activity was found in a peak eluting at a Kay of 0.350 which corresponded to an apparent molecular weight of 67 kDa. on this column (FIG. 2). The fractions containing this peak were pooled, dialysed against the ion-exchange starting buffer and chromatographed on a Mono-S column. Cofactor activity was found in a late peak eluting at approximately 0.5M NaCl (FIG. 3).

Figure 4:
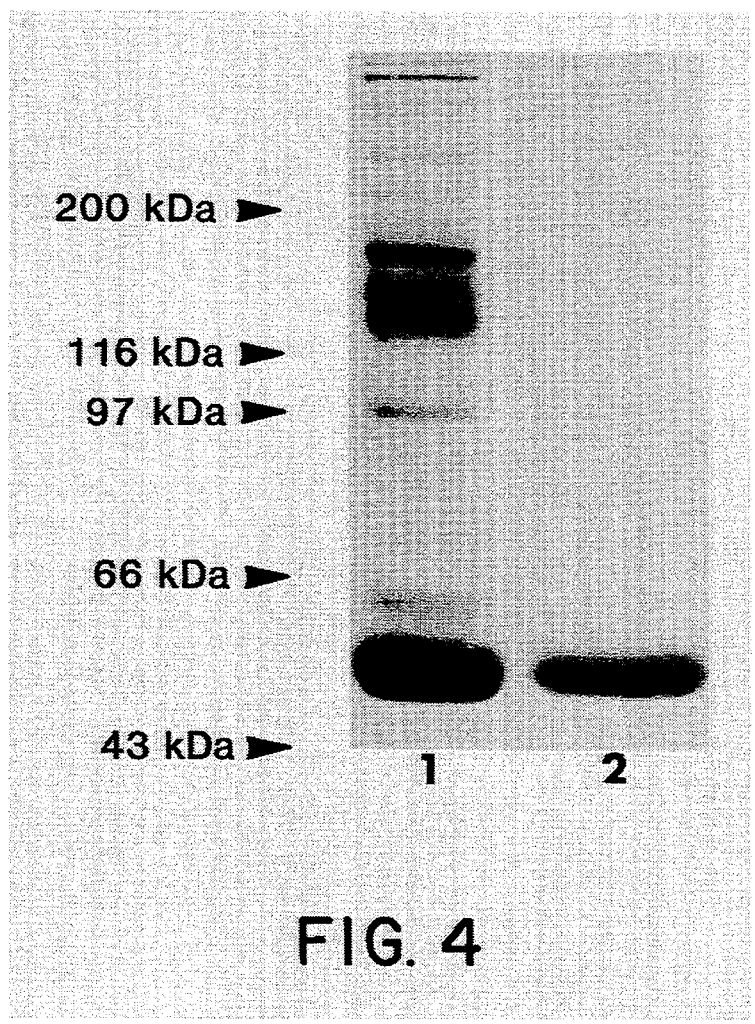
FIG. 4 illustrates SDS-PAGE on a 5–15% linear gradient gel under non-reducing conditions stained with Coomassie Blue. Lane 1: Eluant from CL affinity column chromatography of aCL antibody positive plasma, containing a broad band of IgG-aCL (150 kDa) and cofactor (50 kDa). Lane 2: Purified cofactor obtained from normal plasma following sequential CL affinity, gel-filtration (FIG. 2), and cation-exchange chromatography (FIG. 3).
Figure 5:
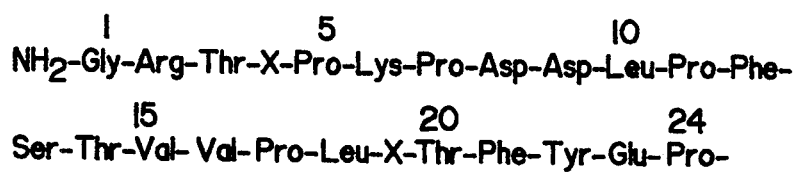
FIG. 5 illustrates amino terminal amino acid sequence of the purified cofactor. X indicates positions in the sequence where residues cannot be identified unambiguously.

The final preparation from the ion-exchange column was found to be highly purified with a single band on SDS-PAGE of apparent molecular weight 50 kDa under both reduced and non-reduced conditions (FIG. 4). This band corresponded to a band previously found in the CL or PS-affinity column eluant when aCL antibody containing plasma was chromatographed on those columns (also shown in FIG. 4). The N-terminal amino acid sequence of the cofactor is shown in FIG. 5. A computer search of current database releases shows this sequence is identical to the amino-terminal sequence of the plasma protein, β-2-glycoprotein-I (β-2GPI) also Known as apolipoprotein H. There were no other proteins which exhibited homology to this sequence except a plasma protein purified by Canfield and Kisiel termed activated protein C binding protein J. Clin. Invest. (1982), 70:1260–1272) which has subsequently been reported identical to β-2GPI.

When plasma containing IgG-aCL antibodies is chromatographed on CL or PS affinity columns, two major protein bands are eluted. One of these is IgG, the other is β-2GPI (FIG. 4). Since β-2GPI was purified from normal plasma using the CL affinity column, it is clear that β-2GPI binds to anionic phospholipid columns both in the presence or absence of aCL antibodies. Yet these antibodies do not bind CL in the absence of β-2GPI. Purified β-2GPI but not aCL bound to a heparin-sepharose column, but aCL antibodies did not bind to this column even in the presence of bound β-2GPI. Thus aCL antibodies recognise β-2GPI bound to anionic phospholipid, but not β-2GPI bound to heparin, indicating both phospholipid and glycoprotein comprises the epitope to which these antibodies are directed. These results suggest that aCL antibodies are directed against either a complex consisting of β-2GPI bound to anionic phospholipid, or a cryptic epitope formed during the interaction of β-2GPI with phospholipid, but not β-2GPI independent of the presence of phospholipid.

EXAMPLE 5

Figure 6A:
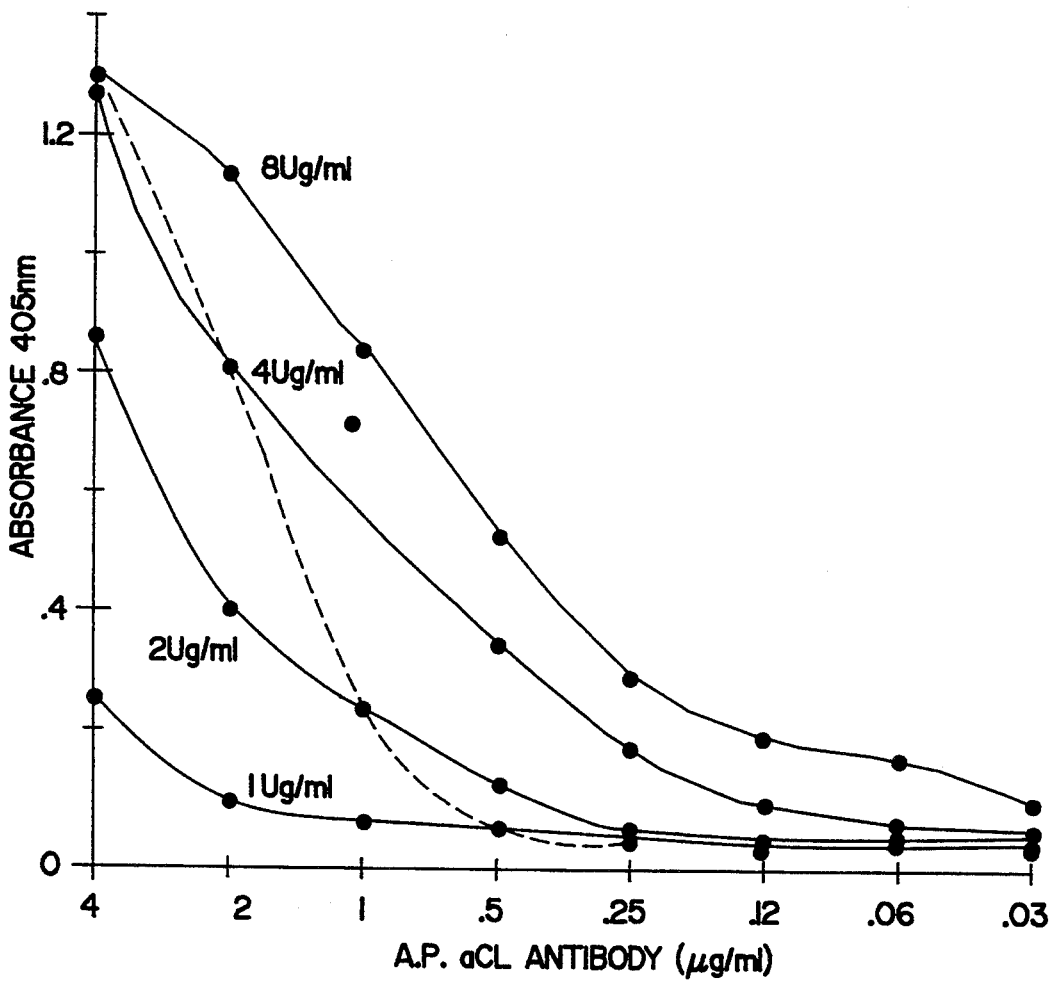
FIG. 6 (a) illustrates: binding in the modified CL-ELISA of serial dilutions of affinity purified aCL antibodies in the presence of serial dilutions of cofactor. Extrapolated binding curve based on dilution of both antibody and cofactor.
Figure 6B:
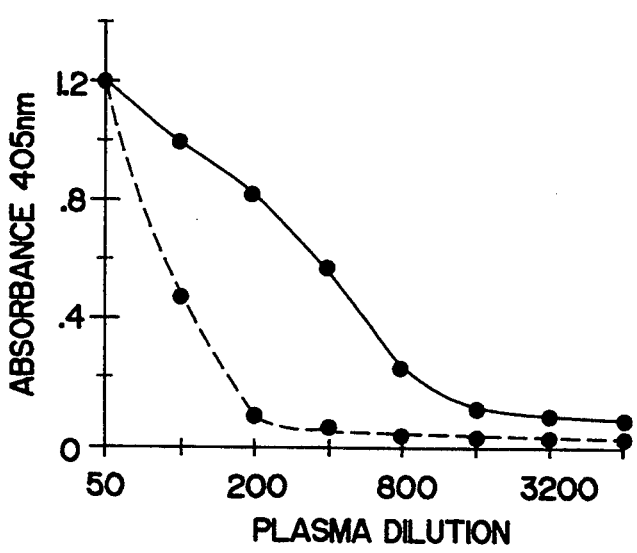
Figure 8:
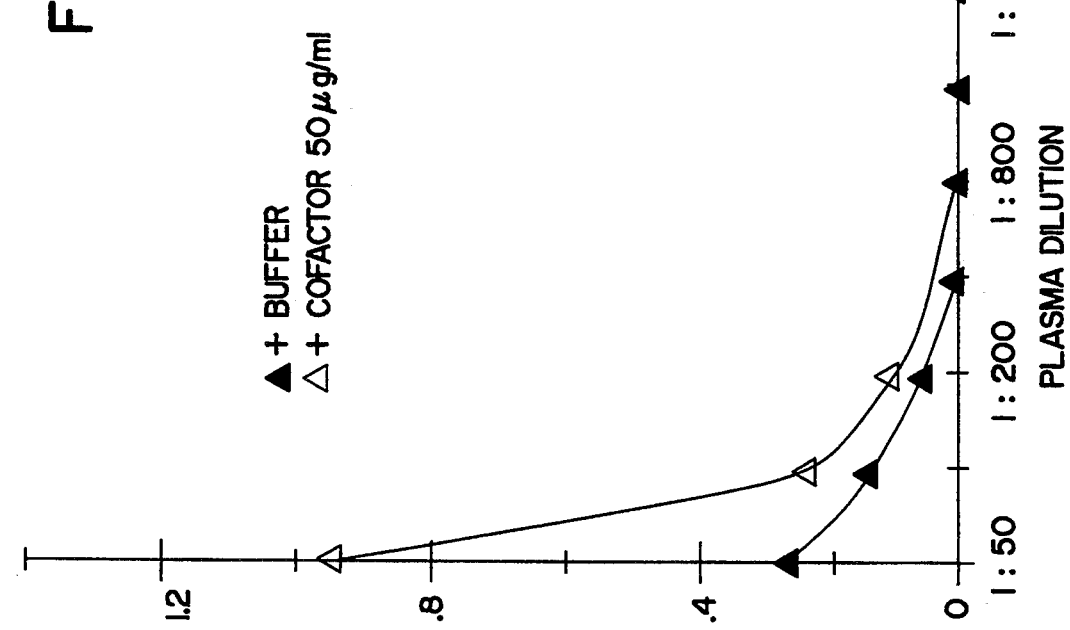
FIG. 8 illustrates binding of serial dilutions of 1 gM, aPL antibodies in the modified CL-ELISA, in buffer or in the presence of 50 μg/ml of cofactor.
Figure 7:
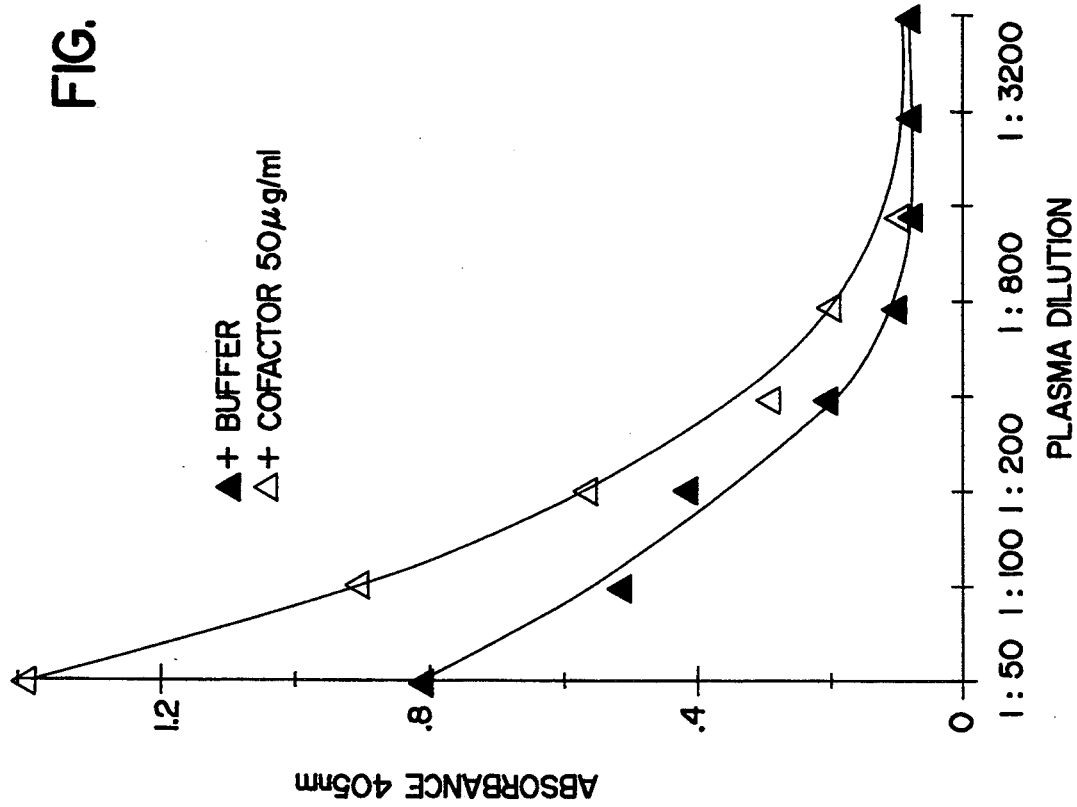
FIG. 7 illustrates binding of serial dilutions of 1 gG, aPL antibodies in the modified CL-ELISA, in buffer or in the presence of 50 μg/ml of cofactor.

Interaction between purified β-2GPI and affinity purified aCL antibodies in the modified CL-ELISA Since affinity purified aCL antibodies do not bind CL in the modified CL-ELISA unless β-2GPI is present (FIG. 1), the binding of sequential dilutions of the antibody was examined, in the presence of sequential dilutions of glycoprotein, purified as described above. These results are shown in FIG. 6a. In the presence of 8 ug/ml β-2GPI, serial dilutions of aCL antibody show a binding curve typical of that seen with the standard CL-ELISA. With increasing dilutions of β-2GPI binding decreases dramatically at all dilutions of antibody with virtually no binding when the glycoprotein is reduced to 1 ug/ml. The broken line indicated in figure 6a accounts for serial dilution of both factors. Dilution of aCL antibody positive plasma is shown in FIG. 6b. The solid line shows the familiar binding curve in a standard CL-ELISA where the presence of ABS ensures adequate cofactor at all antibody dilutions. The broken line shows the binding curve when aCL antibody positive plasma is diluted in the modified CL-ELISA. There is virtually no binding of antibody once plasma is diluted to 1:200 corresponding to a β-2GPI level of approximately 1 ug/ml.

The modified CL-ELISA proved to be a convenient system to examine the cofactor effect in more detail. The action of β-2GPI on aCL antibody binding to CL was found to be dose dependent with a steep dilution effect, such that there was virtually no antibody binding at any dilution when β-2GPI was present at 1 ug/ml or less (FIG. 6a). Since the normal plasma level of β-2GPI is 200 ug/ml, this figure corresponded exactly to the results of diluting aCL antibody positive plasma in the modified CL-ELISA, where there was a rapid drop off in binding which became negative at 1:200 dilution, or at a β-2GPI level of 1 ug/ml, despite the presence of appreciable amounts of aCL antibody (FIG. 6b).

EXAMPLE 6

Heparin Affinity Chromatography

Affinity purified aCL antibodies did not bind to a heparin-sepharose affinity column with approximately 60% of the applied aCL antibody recovered in the fall-through fractions, but no antibody was eluted with 1M NaCl. Purified β-2GPI bound to the heparin-sepharose when applied to the column. When a mixture of affinity purified aCL antibodies and purified β-2GPI was infused through the heparin-sepharose column, the fall-through contained aCL but not β-2GPI and the eluted protein contained β-2GPI but not aCL. When plasma containing aCL antibodies was infused through heparin-sepharose, the fall-through fractions contained equivalent quantities of aCL antibody to the applied plasma, but the eluted protein contained β-2GPI but not aCL antibody.

TABLE 1

Chromatography of aCL antibody containing ion-exchange fractions on CL-affinity column

| Sample | Amount of aCL Antibody | |
|---|---|---|
| | Total Applied | Fall Through |
| I.E. # | 105 units | 101 units (96%)[1] |
| I.E. # + Normal Pl.[2] | 120 units | 80 units (66%) |
| I.E. # + Adsorb Pl. | 120 units | 90 units (75%) |
| I.E. # + β-2GPI[3] | 122 units | 32 units (26%) |

I.E. #, Ion-exchange fraction; Pl, Plasma., Adsorb, AlOH$_3$ adsorbed.
[1] % of total applied aCL antibody recovered in fall-through
[2] 1 ml plasma added to 10 mls I.E. #
[3] 400 ug β-2GPI (equivalent to 2 mls plasma) added to 10 mls I.E. #

The finding that aPL antibodies are directed against an antigen that includes β-2GPI opens new avenues to our understanding of these autoantibodies. It provides an explanation for aPL antibodies binding equally well to all anionic phospholipids despite varying structures. Additionally, since β-2GPI appears to inhibit the intrinsic pathway of coagulation and ADP dependent platelet aggregation, these findings raise the possibility that aPL antibodies interfere with β-2GPI function in-vivo, thereby predisposing to a prothrombotic diathesis. Furthermore, if β-2GPI binds anionic macromolecules, this could include those derived from infectious organisms. Foreign antigen complexed with β-2GPI could be the immunogenic stimulus for the production of aPL antibodies, these being a well recognised occurrence in a number of infectious diseases.

EXAMPLE 7

Samples

Blood was collected via venipuncture into tubes containing 1/10th final volume 0.11M tri-sodium citrate, inverted 2-3 times and centrifuged at 2500 g for 15 minutes. The plasma was aspirated and then filtered through a Millipore Millex GS 22 μM filter to remove any platelet dust and stored at −20° C.

Plasma or serum samples from patients with hepatitis A, tuberculosis, infectious mononucleosis, malaria and syphilis were obtained from other institutions.

Standard anticardiolipin antibody assay

Samples were assayed for the presence of aCL antibodies using an enzyme linked immunoassay as previously described[1] and as modified by McNeil et at[2]. Samples were assayed at a dilution of 1:50 Goat anti-human IgG, IgM or IgA specific and/or polyvalent alkaline phosphatase-conjugated immunoglobulins were used as second antibodies (Sigma). When using polyvalent or IgA second antibody, serial dilutions of a known positive plasma were included on each plate. The aCL level of the test samples was expressed in aCL units, with 100 units being the absorbance at 405 nm of the positive sample at 1:50 dilution. When using IgG or IgM specific second antibody, dilutions of positive samples calibrated against Rayne Institute standards (provided by St. Thomas Hospital, London) were included on each plate. The aCL level was read from the reference sera using a log-log plot and expressed in GPL or MPL units (IgG phospholipid or IgM phospholipid units, where one unit corresponds to the activity of 1 μg of affinity purified aCL) respectively[3]. Samples were considered aCL positive if the levels recorded were more than three standard deviations above the mean of 16 controls.

Ion-exchange chromatography

Plasma samples (0.5 ml) were dialysed against the starting buffer (0.05M acetate 0.05M NaCl pH 4.8) then centrifuged at 5000 g for 5 minutes prior to being applied to a Pharmacia Mono-S HR 5/5 cation exchange column at a flow rate of 0.5 ml/minute, using a Pharmacia FPLC system. The buffers, flow rates and gradient conditions were as previously described[18]. The absorbance was monitored at 280 nm and 1 ml fractions collected.

Each fraction was then assayed for aCL antibodies at a 1/5 dilution using the standard aCL-ELISA described above.

Modified CL ELISA

The above standard CL ELISA was modified as described in Australian Patent Application No. PJ9549, the contents of which are incorporated herein by cross-reference. Briefly, wells are blocked with a 0.3% gelatine/1% Milk powder (Diploma)/phosphate buffered saline (0.01M phosphate 0.15M saline pH 7.3) (PBS) solution instead of 10% Adult bovine serum (ABS)/PBS. Samples were diluted in 0.3% gelatine/PBS and the second antibody in 1% bovine serum albumin (BSA)/PBS, instead of 10% ABS/PBS which is the diluent in all of the steps of the standard CL ELISA.

Effect of purified β$_2$-GPI on binding of aCL antibodies in the modified CL ELISA Ion-exchange fractions that were found to be positive in the standard CL ELISA were assayed in the presence and absence of purified β$_2$-GPI (8 μg/ml) in the modified CL-ELISA system. Purified β$_2$-GPI was obtained as previously described in PJ9549.

Radio-Immunoassay for β$_2$-GPI

A solid phase RIA using $^{125}$I-β$_2$-GPI and polyclonal rabbit antibody to β2-GPI developed by two of the inventors and others[4] was used to assay fractions from the ion-exchange column. The level of β$_2$-GPI in each sample was read from a standard curve using a 4 parameter logistic curve fitting program[5]. The sensitivity of the RIA is 75 ng/ml[4].

Results aCL ELISA of plasma

Of the subjects studied, 23 patients 1,ad a diagnosis of infection (6 syphilis, 9 malaria, 2 hepatitis A, 2 tuberculosis and 4 infectious mononucleosis) and 12 patients had a diagnosis of autoimmune disease (7 primary Antiphospholipid Syndrome (PAPS) and 5 Systemic Lupus Erythematosus (SLE)). Tables 2 and 3 are a summary of the clinical characteristics and aCL status of the patients studied. The range of values and isotope distribution was variable. Patients with infections were predominantly positive For IgG (syphilis), IgM (infectious mononucleosis and tuberculosis) and IgG,M and A (malaria and hepatitis A), whereas patients with a diagnosis of PAPS or SLE were more evenly represented in all three isotypes.

Ion-exchange chromatography of plasma

Figure 9:
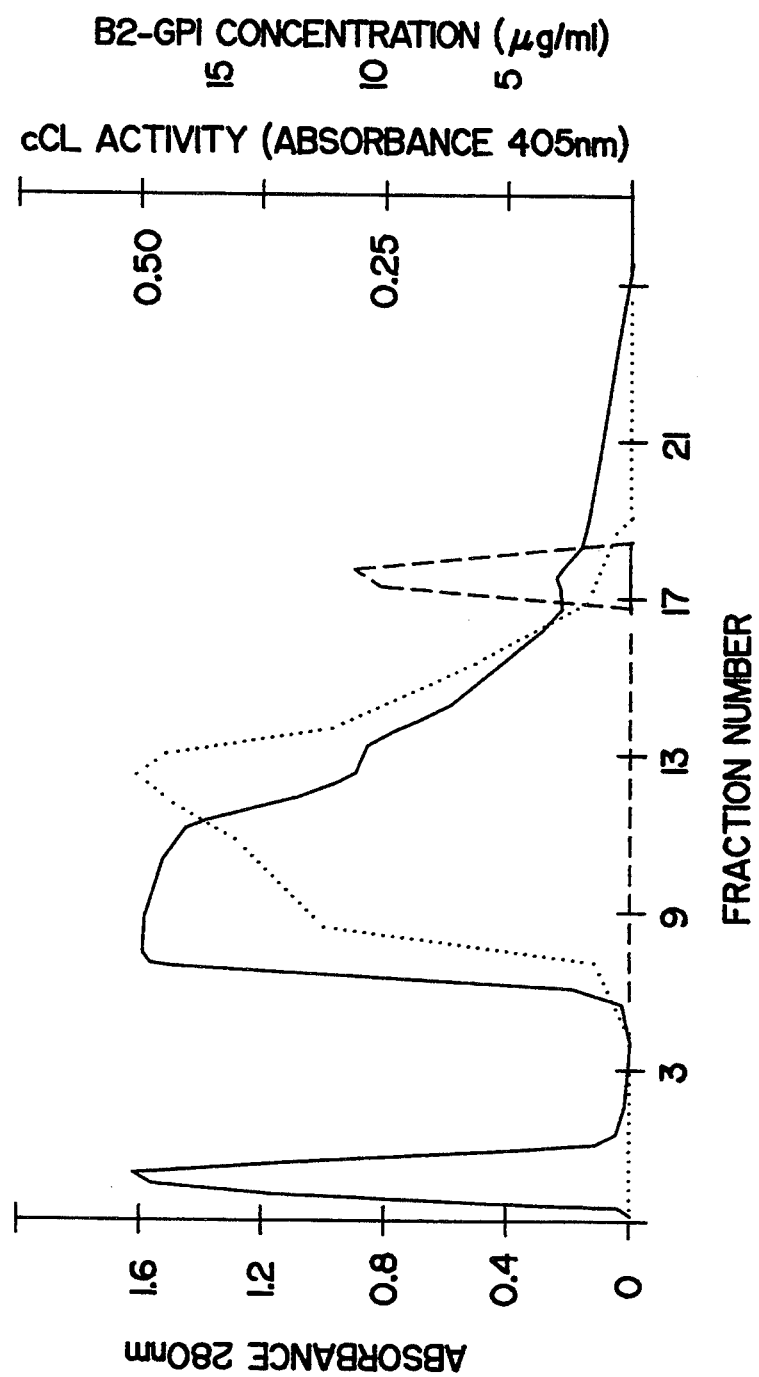
FIG. 9 shows a typical profile of ion-exchange chromatography performed on a dialysed plasma sample from a patient with anticardiolipin antibodies, solid line=absorbance at 280 nm, dotted line=aCL activity (absorbance 405 mm), dashed line=$\beta_2$-GPI (μg/ml)

As previously described[5], plasma containing aCL antibodies can be separated into subgroups by cation-exchange chromatography. As shown in FIG. 9, which illustrates a typical ion-exchange profile of patient plasma, $\beta_2$-GPI eluted as a single peak (fractions 17 & 18) separate from aCL activity which eluted in earlier fractions.

It has been previously reported that the recovery of aCL activities during ion-exchange chromatography using the same procedure to be greater than 70%[6].

Binding of aCL antibody-containing ion-exchange fractions in the modified CL ELISA in the presence and absence of purified $\beta_2$-GPI The results of the binding of aCL antibodies from ion-exchange fractions in the modified CL-ELISA system are summarised in FIGS. 10(A–B) and 11(A–D).

Patients with infection associated aCL

Without exception, ion-exchange fractions from patients whose aCL antibodies were associated with infection, bound CL in the modified CL ELISA system without the addition of $\beta_2$-GPI. Addition of $\beta_2$-GPI resulted in moderate inhibition of aCL binding. Binding of aCL to Cl was reduced by an average of 34% for IgG, 33% for IgM and 46% for IgA.

Patients with autoimmune associated aCL

When aCL antibody containing fractions from patients with autoimmune disease were tested in the modified IgG CL-ELISA, five of the eight patients (#'s 24, 26, 27, 28 & 30) did not bind in the absence of $\beta_2$-GPI (FIG. 11A). When $\beta_2$2GPI was added, a dramatic increase in binding occurred (mean absorbance at 405 nm $+/-$SD (n=5) with no $\beta_2$-GPI present=$0.072+/-0.058$; with $\beta_2$-GPI present=$1.186+/-0.430$) (FIG. 11B). Two of the remaining three patient samples (#'s 29 and 31) displayed significant binding without added $\beta_2$-GPI, and a small increase in binding when $\beta_2$-GPI was added. Only one patient sample (#25) showed significant binding without $\beta_2$-GPI and inhibition of binding when $\beta_2$-GPI was added (FIGS. 11A and 11C).

The autoimmune group were generally only weakly positive for IgM-aCL and only four of the samples generated ion-exchange fractions with enough IgM aCL activity to test in the modified aCL-ELISA. One patient sample (#29) only bound CL when $\beta_2$-GPI was added. Three patient samples displayed some binding to CL without $\beta_2$-GPI, two of which showed a small increase in binding with added $\beta_2$-GPI (#25 and #27) and one which showed mild inhibition (#24)(data not shown).

In the IgA modified CL ELISA, four of the ion-exchange purified aCL fractions (from patients #24, 25, 26 & 27) showed little or no binding the absence of $\beta_2$-GPI, and significantly enhanced binding when $\beta_2$-GPI was added (mean absorbance at 405 nm $+/-$SD without $\beta_2$-GPI=$0.10+/-0.03$, with added $\beta_2$-GPI=$0.50+/-0.25$). Four patients showed moderate binding in the absence of $\beta_2$-GPI. Of these patients, two (#29 and #30) displayed enhanced binding with added $\beta_2$-GPI, one (#28) showed little change and one (#31) showed moderate inhibition of binding (Figs. 11B and 11D).

aCL-positive ion-exchange fractions from 4 patients with autoimmune disease were previously tested in a CL-ELISA using polyvalent second antibody. All four patients (#'s 32, 33, 34 & 35) showed no binding in the absence of $\beta_2$-GPI but a dramatic increase in binding in the presence of $\beta_2$-GPI (mean absorbance $+/-$SD=$0.05+/-0.05$ without $\beta$2-GPI, and $0.40+/-0.09$ with $\beta$2-GPI: (FIGS. 11A and 11C).

Discussion of Results

Figure 10A:
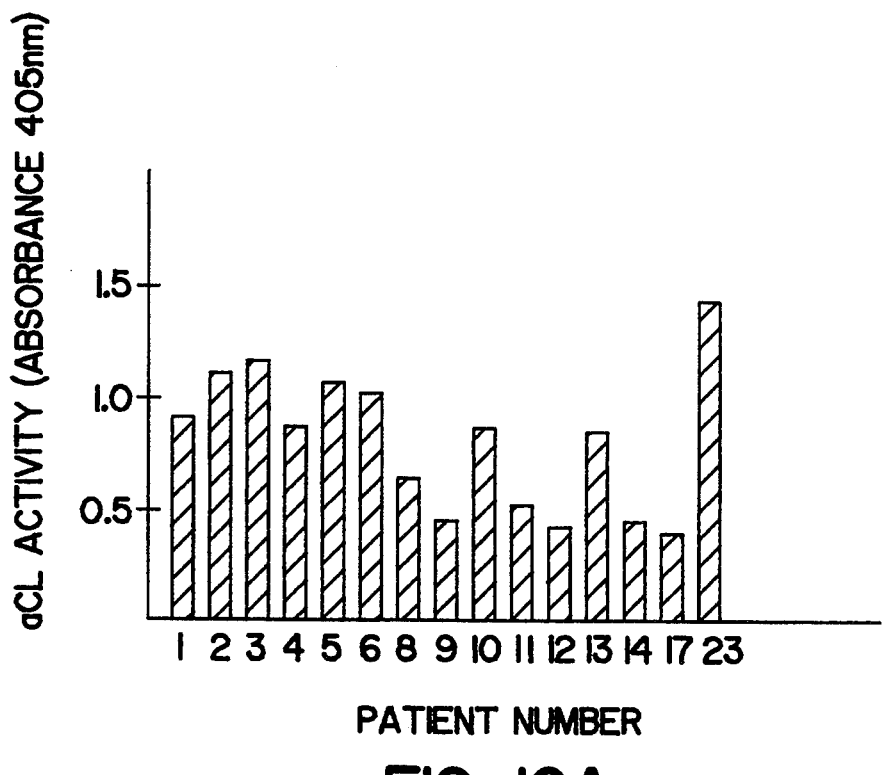
FIGS. 10A and 10B shows results of modified CL-ELISA (IgG) performed on patients with aCL associated with infection. A=no B2-GPI added, B=$\beta_2$-GPI added.
Figure 10B:
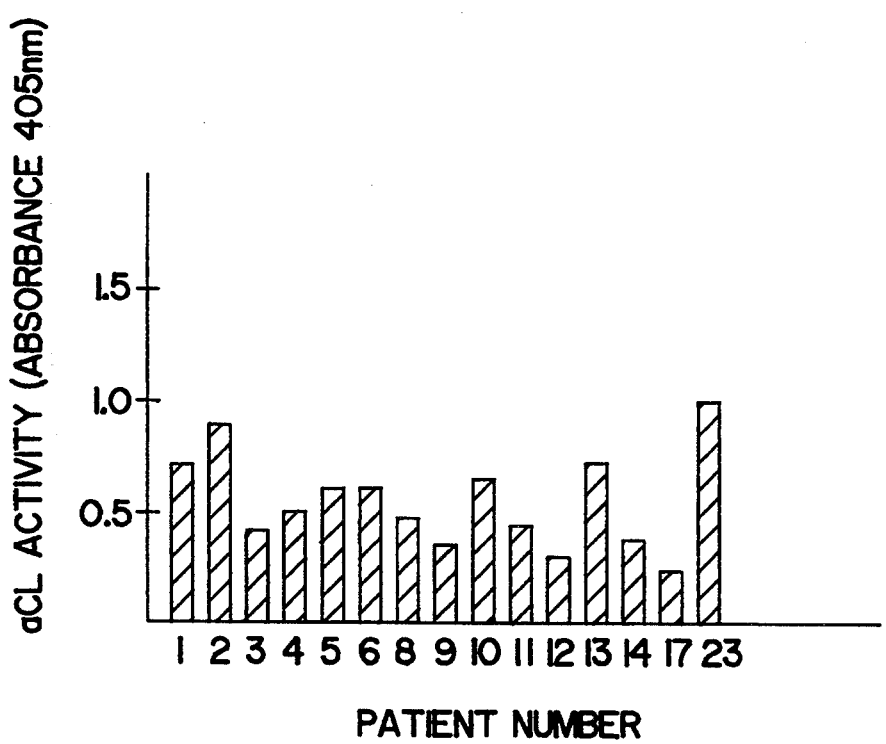

In Example 7 ion-exchange purified aCL antibodies from patients with autoimmune disease and a variety of Infections have been examined Without exception aCL antibodies from patients with infections bound CL in the modified ELISA without the need for added $\beta_2$-GPI. In all samples tested from patients with infections addition of $\beta_2$-GPI resulted in a moderate reduction of aCL binding in the modified ELISA (FIGS. 10A and 10B).

In contrast, ion-exchange purified aCL antibodies (in at least one isotype) from eleven of twelve patients with autoimmune disease, required the presence of $\beta_2$-GPI to bind CL. In one patient with autoimmune disease the IgG-aCL antibody did not require the presence of $\beta_2$-GPI to bind CL but the IgA-aCL in the same patient did. This distinct difference in phospholipid binding characteristics in the absence of $\beta_2$-GPI clearly suggests that there are subtypes of aCL antibodies in individual patients. There appears to be not only differences between the requirements of infection associated aCL and SLE/PAPS associated aCL to bind CL, but also different subsets of aCL within the latter group, with different isotypes having different binding specificities.

The modified CL-ELISA proved to be a convenient system to examine the $\beta_2$-GPI requirement of the purified aCL antibodies binding to CL. There was little or no binding of aCL antibodies to uncoated wells in the modified CL-ELISA (results not shown). The effect of $\beta_2$-GPI on aCL binding to CL is dose dependent, such that there was no binding of aCL antibody at any dilution when $\beta_2$-GPI is present at 1 $\mu$g/ml or less. The RIA for $\beta_2$-GPI is sensitive down to 75 ng/ml[4], so the ion-exchange purified aCL antibody fractions do not contain concentrations of $\beta_2$-GPI that would support binding to CL.

The fact that aCL that bind $\beta_2$-GPI have only been found in the SLE/PAPS group may have important clinical implications. It is in this group of patients that thrombo-embolic complications have been reported. Most reports indicate that these complications are not found in patients whose aCL are associated with syphilis or other infective causes[7]. In an extensive review of the literature[8] the present inventors found that the incidence of thrombotic complications in SLE patients with aCL is 42%. When non-SLE but aCL positive patients are included, the incidence drops to 31%. This may be due to the inclusion of groups that are at low risk of thromboses due to a specific non-thrombotic sub-class of aCL i.e., of the infective type. In addition, aCL antibodies of the infective type may occur in patients with autoimmune disease as shown in the present study.

The mechanism by which antibodies directed against either a $\beta_2$-GPI/phospholipid complex or $\beta_2$-GPI alone may predispose to clotting disorders has not been determined. However $\beta_2$-GPI has been previously reported to inhibit both ADP-mediated plateletaggregation[9] and the prothrombinase activity of activated platelets[10].

In conclusion, one of the methods of the present invention demonstrated that aCL antibodies that bind $\beta_2$-GPI (either alone or as a phospholipid complex) are only found in an autoimmune group of patients. aCL antibodies associated with infections did not require $\beta_2$-GPI to bind CL in the solid phase ELISA. This may be clinically important as clotting disorders have commonly been reported in autoimmune associated aCL but not with aCL associated with infection.

Potentiation of $\beta_2$-GPI with an Autoimmune Serum

Figure 12:
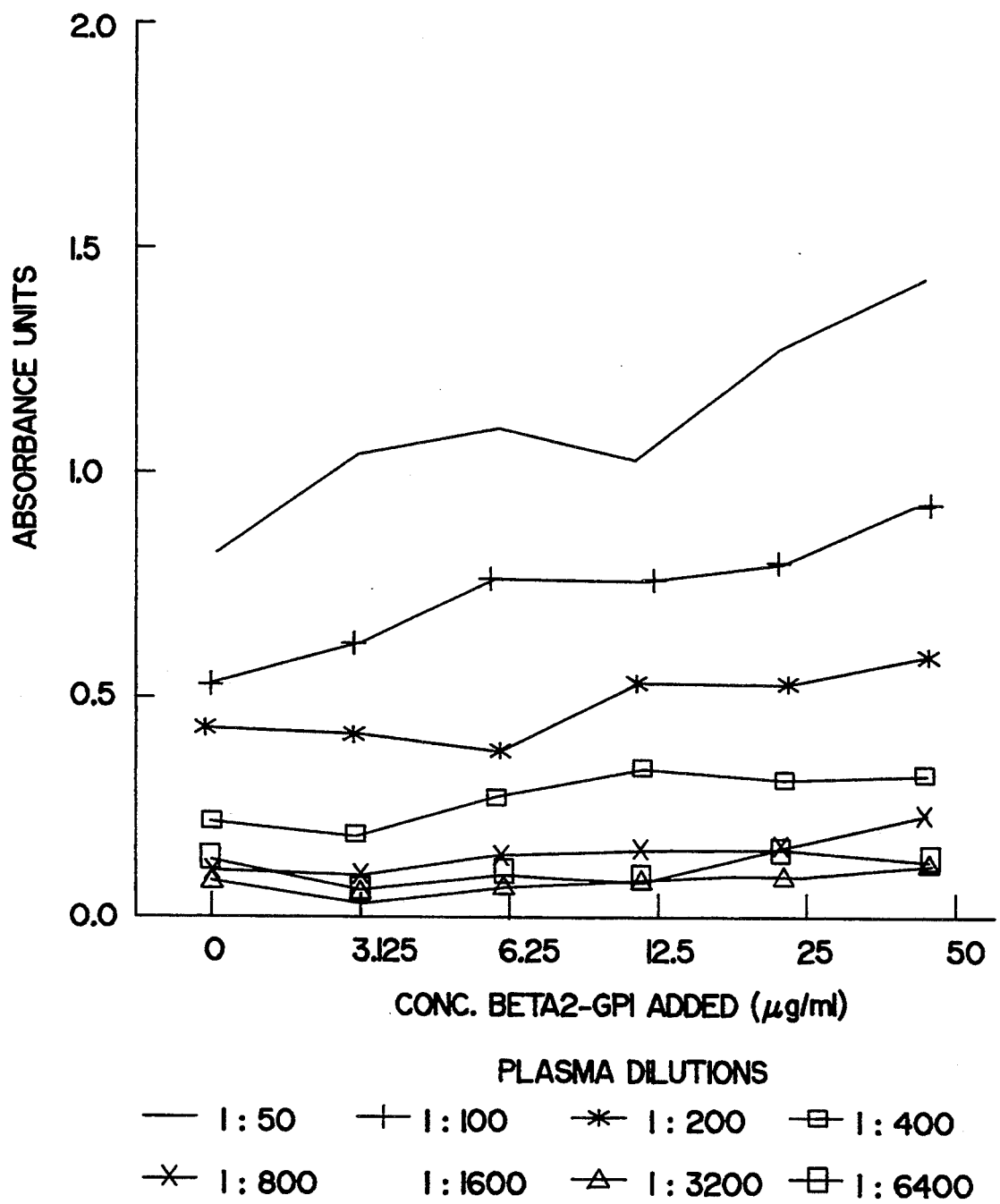
FIG. 12 shows results for the potentiation of $\beta_2$-GPI with an autoimmune serum.

In FIG. 12 results for the potentiation of $\beta_2$-GPI with an autoimmune serum are shown. Plasma was obtained from a patient with autoimmune disease and dilutions were made from 1 in 50 to 1 In 6400. Antiphospholipid antibodies were determined using a cardiolipin ELISA assay without adding $\beta_2$GPI and with increase in concentrations from 3.125 micrograms per ml to 50 micrograms per ml. In this instance, the ELISA assay was a standard one where 10% adult bovine serum was added to block the plates and the samples were diluted in 10% adult bovine serum PBS. From FIG. 12 It Is clear that even in the presence of the bovine serum potentiation Is evident at dilutions of plasma down to 1 in 400.

INDUSTRIAL APPLICABILITY

The methods of the first and second embodiments of the present invention are of particular use for detecting whether antiphospholipid antibodies or negatively charged phospholipids are present in a sample, respectively. The methods of the fifth and sixth embodiments of the present invention are of particular use for for determining whether antiphospholipid antibodies in a sample are antibodies to an autoimmune disease or antibodies to an infectious disease or whether antiphospholipid antibodies to an autoimmune disease and antiphospholipid antibodies to an infectious disease are present in a sample, respectively.

REFERENCES

1. Gharavi A. E., Harris E. N., Asherson R. A., Hughes G. R. V. Anticardiolipin antibodies:isotype distribution and phospholipid specificity. *Ann. Rheum. Dis.* 1987;46:1-6.
2. McNeil H. P., Chesterman C. N., Krilis S. A. Binding specificity of lupus anticoagulants and anticardiolipin antibodies. *Thromb. Res.* 1988;52: 609-619.
3. Harris E. N., Gharavi A. E., Patel S. P., Hughes G. R. V. Evaluation of the anticardiolipin antibody test: report of an international workshop held Apr. 4, 1986. *Clin Exp Immunol* 1 1987;68:215-222.
4. McNeil H. P., Wei Shi, Chesterman C. N., Krilis S. A. Elevated plasma $\beta_2$-GPI levels in patients with anticardiolipin antibodies.(submitted).
5. Rodbard D , Munsa P. J. *Nashville: Biomedical Computing Information:*1984.
6. McNeil H. P., Chesterman C. N., Krilis S. A. Anticardiolipin antibodies and lupus anticoagulants comprise separate antibody subgroups with different phospholipid binding characteristics. *Br J Haematol*1989;73: 506-513.
7. Harris E. N., Gharavi A. E., Loizou S., et al. Cross reactivity of antiphospholipid antibodies. *J. Clin. Lab. Immunol.*1985;16: 1-6.
8. McNeil H. P., Chesterman C. N., Krilis S. A. Immunology and clinical importance of antiphospholipid antibodies. *Adv. Immunol.*1990;49: (in press).
9. Nimpf J. , Wurm H., Kostner G. M. Interactions of $\beta_2$-Glycoprotein-I with human blood platelets: Influence upon the ADP-induced aggregation. *Atherosclerosis.*1987;63: 109-114.
10. Nimpf J., Bevers E. M., Bomans P. H. H., et al. Prothrombinase activity of human platelets is inhibited by $\beta_2$-Glycoprotein-I. *Biochem. Biophys. Acta.* 1986;884: 142-149.

TABLES 2 and 3: Summary of the clinical characteristics and aCL status of the patients studied.

TABLE 2

Aborbance (405 nm) in the standard CL ELISA of Plasma samples from patients with infections

| Patient # | Diagnosis | IgG | aCL IgM | IgA |
|---|---|---|---|---|
| 1 | Syphilis | + | − | ND |
| 2 | " | + | − | ND |
| 3 | " | + | − | ND |
| 4 | " | + | − | ND |
| 5 | " | + | − | ND |
| 6 | " | + | − | ND |
| 7 | Malaria | − | + | − |
| 8 | " | + | − | − |
| 9 | " | + | + | − |
| 10 | " | + | + | + |
| 11 | " | + | − | + |
| 12 | " | + | + | − |
| 13 | " | + | + | + |
| 14 | " | + | − | + |
| 15 | " | − | + | + |
| 16 | Hepatitis A. | − | + | − |
| 17 | " | + | + | + |
| 18 | Tuberculosis | − | + | − |
| 19 | " | − | + | − |
| 20 | Infectious mononucleosis | − | + | − |
| 21 | " | − | + | − |
| 22 | " | − | + | + |
| 23 | " | + | + | + |

KEY
ND = not determined
− = negative
+ = positive (> mean + 3 sd of 16 controls, IgG = 0.21, IgM = 0.29, IgA = 0.16 [absorbance 405 nm])

TABLE 3

Absorbance at 405 nm in the standard CL ELISA of plasma samples from patients with autoimmune disease

| Patient # | Diagnosis | Thrombosis. | IgG | aCL IgM | IgA |
|---|---|---|---|---|---|
| 24 | SLE | Y | + | + | + |
| 25 | SLE | N | + | + | + |
| 26 | SLE | Y | + | + | + |
| 27 | PAPS | Y | + | + | + |
| 28 | PAPS | Y | + | + | + |
| 29 | PAPS | Y | + | + | + |
| 30 | PAPS | Y | + | + | + |
| 31 | PAPS | Y | + | + | + |
| | | | | polyvalent | |
| 32 | PAPS | Y | | + | |
| 33 | PAPS | Y | | + | |
| 34 | SLE | N | | + | |
| 35 | SLE | N | | + | |

Key
PAPS = Primary Antiphospholipid Syndrome
SLE = Systemic Lupus Erythematosis
Y = YES
N = NO

We claim:

1. A method for determining whether antiphospholipid antibodies are present in a sample from a patient suspected of having an infectious and/or autoimmune disease, comprising:
   contacting the sample with a negatively charged phospholipid and with $\beta$-2-glycoprotein-I; and
   determining whether any antiphospholipid antibodies have bound to the contacted phospholipid and $\beta$-2-glycoprotein-I, wherein detection of binding of antiphospholipid antibodies to the phospholipid and $\beta$-2-glycoprotein-I, is indicative that antiphospholipid antibodies are present in the sample.

2. The method of claim 1 wherein said negatively charged phospholipid is selected from the group consisting of cardiolipin, phosphatidyl inosityl, phosphatidyl serine, phosphatidyl glycerophosphate, and phosphatidic acid.

3. The method of claim 1 wherein said negatively charged phospholipid is immoblized on a solid phase selected from the group consisting of affinity column packing material, microtitre plate, dipstick, gel, matrix, liposomes and micelles.

4. The method of claim 1 wherein said β-2-glycoprotein-I is in substantially pure form.

5. The method of claim 1 wherein said β-2-glycoprotein-I is immobilized on a solid phase selected from the group consisting of affinity column packing material, microtitre plate, dipstick, gel, matrix, liposomes and micelles.

6. A kit for use in the method of claim 1, comprising:
   a) β-2-glycoprotein-I,
   b) a negatively charged phospholipid and
   c) labeled anti-human secondary antibodies for detecting binding of antiphospholipid antibodies present in the sample to the β-2-glycoprotein-I and the negatively charged phospholipid.

7. The kit of claim 6 wherein said negatively charged phospholipid is selected from the group consisting of cardiolipin, phosphatidyl inosityl, phosphatidyl serine, phosphatidyl glycerophosphate, and phosphatidic acid.

8. The kit of claim 6 wherein said negatively charged phospholipid is immobilised on a solid phase selected from the group consisting of affinity column packing material, microtitre plate, dipstick, gel, matrix, liposomes and micelles.

9. The kit of claim 6 wherein said β-2-glycoprotein-I is in substantially pure form.

10. A method for determining the presence or the amount of an anticardiolipin antibody in a sample, comprising:
    contacting the sample with cardiolipin and β-2-glycoprotein-I; and
    determining the presence or the amount of the anticardiolipin antibody which has bound to the contacted cardiolipin and β-2-glycoprotein-I.

11. The method of claim 10, wherein the cardiolipin is immobilized on a microtitre plate.

12. The method of claim 10, wherein the cardiolipin together with β-2-glycoprotein-I are immobilized on a microtitre plate.

13. The method of claim 10, wherein β-2-glycoprotein-I is contained in a dilution liquid used for diluting the sample.

14. The method of claim 10, wherein β-2-glycoprotein-I is used in an amount of more than 1 μg/ml.

15. The method of claim 10, wherein β-2-glycoprotein-I is derived from a warm-blooded animal.

16. The method of claim 10, wherein the sample is human blood or fraction thereof.

17. A kit for use in the method of claim 10, comprising:
    a) β-2-glycoprotein--I,
    b) cardiolipin and
    c) labeled anti-human secondary antibodies for detecting binding of anticardiolipin antibodies present in the sample to the β-2-glycoprotein-I and the cardiolipin.

18. The kit of claim 17, wherein the cardiolipin is immobilized on a microtitre plate.

19. The kit of claim 17, wherein β-2-glycoprotein-I is contained in a dilution liquid used for diluting a sample.

20. The kit of claim 17, wherein β-2-glycoprotein-I is derived from a warm-blooded animal.

* * * * *